United States Patent [19]

Butler

[11] Patent Number: 4,827,043

[45] Date of Patent: May 2, 1989

[54] IMPURITY REMOVAL FROM CARBON MONOXIDE AND/OR HYDROGEN-CONTAINING STREAMS

[75] Inventor: Gerald E. Butler, Longview, Tex.

[73] Assignee: Eastman Kodak Company, Rochester, N.Y.

[21] Appl. No.: 146,756

[22] Filed: Jan. 22, 1988

[51] Int. Cl.⁴ .................. C07C 45/78; C07C 45/50
[52] U.S. Cl. ............................... 568/492; 568/451
[58] Field of Search ............................ 568/451, 492

[56] References Cited

U.S. PATENT DOCUMENTS

| | | | |
|---|---|---|---|
| 4,143,075 | 3/1979 | Bryant | 260/604 |
| 4,242,284 | 12/1980 | Harris et al. | 568/454 |
| 4,247,486 | 1/1981 | Brewester et al. | 568/454 |
| 4,287,370 | 9/1981 | Harris et al. | 568/454 |
| 4,523,036 | 6/1985 | Cornils et al. | 568/454 |
| 4,577,043 | 3/1986 | Kalbfell | 568/454 |

Primary Examiner—Warren B. Lone
Attorney, Agent, or Firm—S. E. Reiter; William P. Heath, Jr.

[57] ABSTRACT

Disclosed is a process for the purification of carbon monoxide and/or hydrogen-containing gas streams employed for chemical conversion reactions by contacting such gas feed streams with the oxygenated organic reaction products obtained in the subject chemical conversion reaction.

20 Claims, 1 Drawing Sheet

IMPURITY REMOVAL FROM CARBON MONOXIDE AND/OR HYDROGEN-CONTAINING STREAMS

This invention relates to the purification of gas feed streams comprising carbon monoxide and/or hydrogen. In a particular aspect, this invention relates to an integrated process wherein the reaction product stream is employed to purify the feed gases employed for a chemical conversion process.

BACKGROUND OF THE INVENTION

Many chemical conversions are known which employ hydrogen and/or carbon monoxide-containing gases. These gases frequently contain small amounts of impurities which are detrimental to the desired chemical conversions. As a result, numerous treatments have been developed to remove such impurities such as oxygen, elemental sulfur, organic as well as inorganic sulfur compounds, iron, and the like. Each such impurity removal process introduces added requirements for equipment (e.g., scrubbers, guard beds, and the like), the maintenance thereof, utility consumption, and the like. It would be desirable to eliminate the need for such added equipment and materials as fixed beds containing alumni, zinc oxide, and the like.

Accordingly, a relatively simple, inexpensive means to remove undesirable impurities from carbon monoxide and/or hydrogen-containing feed streams would be of great benefit to numerous chemical conversion reactions.

OBJECTS OF THE INVENTION

An object of the present invention, therefore, is a process for the removal of impurities from carbon monoxide and/or hydrogen-containing feed streams employed for chemical conversion reactions.

Another object of the present invention is a chemical conversion process employing carbon monoxide and/or hydrogen-containing gases wherein deactivating impurites are readily and inexpensively removed from the gaseous feed stream.

These and other objects of the present invention will become apparent upon inspection of the detailed description and appended claims which follow.

STATEMENT OF THE INVENTION

In the accordance with the present invention, I have discovered that the common impurities in carbon monoxide and/or hydrogen-containing feed streams, i.e., oxygen, sulfur, iron, and the like, can be removed by contacting such gas streams with the oxygenated product stream obtained from a process in which the carbon monoxide and/or hydrogen are fed as a co-reactant.

The practice of the present invention allows one to eliminate the need for ancillary gas purification equipment, such as a fixed bed purification column, thereby saving the capital and maintenance costs associated with such equipment. In addition, the invention process enables the efficient recovery and recycle of unreacted gaseous components from the product stream. Moreover, the invention process accomplishes the removal of many undesirable components from the carbon monoxide and/or hydrogen-containing feed streams, including water vapor.

DETAILED DESCRIPTION OF THE INVENTION

Figure 1:
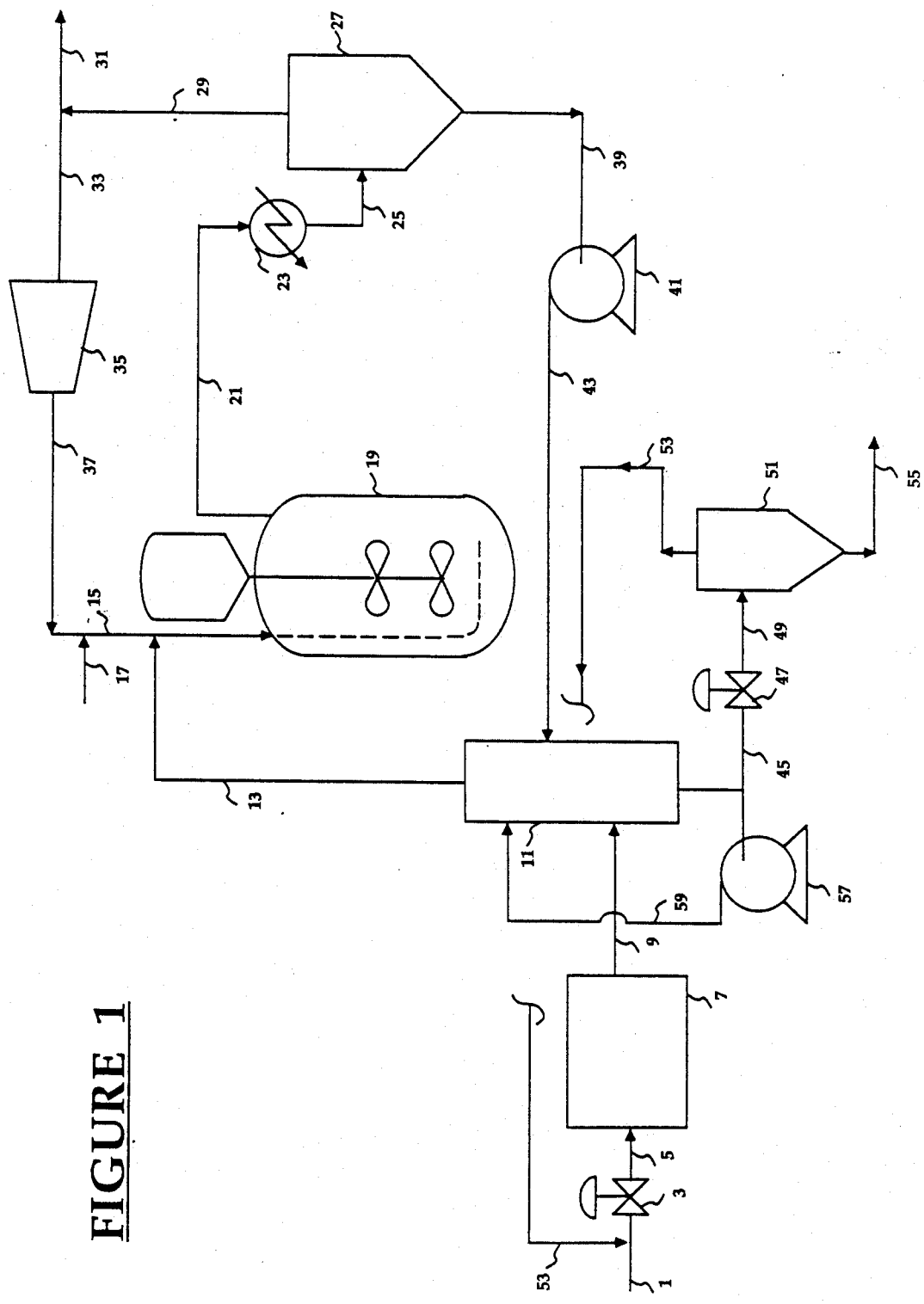
FIG. 1 is a flow diagram of an exemplary scheme incorporating the process of the present invention.

In accordance with the present invention, there is provided a process for purifying a feed gas employed in a chemical conversion process for the production of oxygenated compounds, wherein the feed gas comprises carbon monoxide and/or hydrogen. The invention process comprises intimately contacting the feed gas with at least a portion of the oxygenated product stream obtained from the chemical conversion process prior to introducing the feed gas into the chemical conversion reaction zone. The invention process is applicable to such conversions as the hydroformylation reaction, the Fisher-Tropsch reaction, homologation reaction, anhydride-forming reactions, and the like.

The contacting of feed gas with oxygenated product stream in accordance with the present invention can be carried out under a variety of conditions. For example, the pressure of the contacting can vary from about 7 up to 40 atmospheres. Preferably, pressure of the contacting will be carried out at approximately the same pressure as is being employed for the chemical conversion process. In this way, unreacted feed components for the desired conversion can be stripped from the crude oxygenated product and recycled into the chemical conversion reaction without the need for recompression, cooling, condensation, or the like.

Similarly, the temperature at which the contacting is performed can vary widely, and will be a function of the pressure, the nature of the oxygenated product employed for the contacting, the length of time during which feed gas and oxygenated product are maintained in intimate contact, and the like. The lower temperature employed is determined by the efficiency of impurity removal desired (with contacting at too low a temperature being essentially ineffectual); while at excessively high contact temperatures, substantial quantities of liquid reaction product are stripped from Vessel 11 and returned to the reactor. In addition, excessively high temperatures cause an increased formation of by-products. Typically, temperatures in the range of about 25° up to 100° C. are suitable for the contacting, with temperatures in the range of about 40° up to 65° C. being preferred.

The contact time and ratio of feed gas to liquid oxygenated reaction product can each vary widely. Generally, sufficient time of contact is maintained to allow a major proportion of the feed gas impurities to be absorbed by the liquid reaction product. Similarly most any ratio of feed gas to liquid is suitable, so long as the volume of liquid employed is sufficient to absorb a major proportion of the impurities contained in the feed gas.

Referring now to FIG. 1, the invention will be described with particular reference to the apparatus illustrated therein. The flow of crude feed gases via Line 1 and recycled gases via Line 53 into Compressor 7 is controlled by Valve 3. The combined gas stream is subjected to compression up to the desired reaction pressure then passed through Line 9 into Vessel 11 in which the crude feed gas stream and a portion of reactor effluent are brought into intimate contact with one another.

As employed in this specification, the term "intimate contact" refers to any means by which the gas-liquid interface between crude feed gas and reactor effluent is maximized. Those of skill in the art recognize that this can be accomplished in a variety of ways. For example, the crude feed gas can be passed upwardly in a countercurrent fashion through a body of reactor effluent. Alternatively, crude feed gas can be sparged into a body of reactor effluent. The column dimensions can vary widely and are not believed to be critical. The presence of column packings may increase the efficiency of the contacting operation, as will certain column designs which cause turbulent fluid flow through the column to occur.

Once crude feed gases and reaction product have been intimately contacted, the treated feed gas stream passes via Line 13 and is combined with organic feed stream (introduced via Line 17), with the combined feed streams being introduced into Reactor 19 (via Line 15). After having contacted crude feed gas in Vessel 11, crude oxygenated reaction product is removed from Vessel 11 via Line 45 where product is recycled to Vessel 11 via Pump 57 and Line 59 (in order to control the gas/liquid ratio), or product is controllably delivered to Flash Tank 51 via Valve 47 and Line 49. The gases obtained in the flash tank are recycled via Line 53 and admixed with additional crude feed gas being introduced via Line 1. The crude reaction product obtained from the crude reaction tank is removed via Line 55 and delivered to crude product tank for further manipulation.

Returning now to Reactor 19, reactor volume is maintained fairly constant by removing a vaporous stream overhead via Line 21. The vaporous reactor effluent is passed through Chiller 23 then into Vapor/Liquid Separator 27 via Line 25. Gaseous products are taken overhead via Line 29 and either recirculated to the reaction vessel via Line 33, Recirculator 35, Lines 37 and 15 or, as appropriate, overhead gases are removed from the reaction train via inert Purge Line 31. Liquid product is removed from Vapor/Liquid Separator 27 via Line 39. This material is then pumped via Pump 41 through Line 43 into Vessel 11 where the crude reaction product is contacted with additional quantities of crude feed gas.

As FIG. 1 and the above description of the figure make clear, the oxygenated reaction product itself is used to remove undesirable impurities from the crude feed gas stream. At the same time, unreacted quantities of the organic reactant feed via Line 17 can be stripped from the crude product stream in Vessel 11 and returned directly to the reaction vessel (No. 19) without the need for recompression of such organic feed material.

Exemplary chemical conversion processes contemplated by the present invention include the hydroformylation reaction, the Fischer-Tropsch reaction, homologation reaction, anhydride-forming reactions, and the like. A presently preferred application of the invention process is in the hydroformylation reaction, wherein olefins having 2 up to 20 carbon atoms are converted to aldehydes having n+1 carbon atoms. Preferred olefins are α-olefins having 2 up to 8 carbon atoms. Exemplary hydroformylation reactions include the conversion of propylene to n-butyraldehyde, ethylene to propionaldehyde, butenes to valeraldehydes, as well as conversions of mixed olefins feeds to produce mixed aldehyde products.

The invention will now be described in greater detail by reference to the following non-limiting examples.

EXAMPLE 1

Effect of Temperature on Oxygen Removal

Example 1 shows how the process of the present invention can be employed to remove molecular oxygen from a crude synthesis gas stream using the product liquid of a hydroformylation reaction. A hydroformylation reaction utilizing a rhodium-phosphine catalyst system to produce butyraldehydes was operated at a pressure of 18 bars. The molecular oxygen scrubber employed was a 6-inch diameter by 12 foot tall tower packed with ½-inch stainless steel Pall rings. A ratio of product liquid to crude feed gas of 5.12 gal. of product liquid per standard cubic foot (std. ft.$^3$) of feed gas was maintained, at a feed gas rate of about 187 std. ft.$^3$/hour. When the average temperature of the molecular oxygen scrubber was about 40° C., the average daily phosphine losses to phosphine oxide (caused by the presence of molecular oxygen in the feed gases) were 2.08 percent of the phosphine in the reactor. When the average temperature of the scrubber was increased to 55° C., the average daily phosphine losses to phosphine oxide were reduced to 1.3875 percent of the phosphine in the reactor, for a 34 percent reduction in phosphine losses.

EXAMPLE 2

Effect of Pressure on Oxygen Removal

An 8-inch diameter by 10-foot tall absorption tower filled with ⅜-inch Intalox saddles was used to evaluate absorption of trace quantities of oxygen from a stream of nitrogen using crude butyraldehydes as absorption liquid. In the first test the pressure of the system was 1 bar. An oxygen meter was used to measure oxygen concentration in both the incoming and outgoing nitrogen stream. In the second and third tests the pressure was raised to 7 bar. The temperature for all three tests was 50°–60° C.

The results are shown in Table 1.

TABLE 1

| Test No | Elapsed Time, hr. | Inlet $O_2$ PPM | Outlet $O_2$ PPM | Pressure Bar |
|---|---|---|---|---|
| 1 | 0 | 29 | 18 | 1 |
|  | 1 | 23 | 12 | 1 |
|  | 2 | 13 | 9 | 1 |
| 2 | 0 | 100 | 12.5 | 7 |
|  | 1 | 100 | 2.5 | 7 |
| 3 | 0 | 6.2 | 3.5 | 7 |
|  | 3 | 5.1 | 0.0 | 7 |

The results indicate that $O_2$ will be absorbed at both low pressure and high pressure but that oxygen absorption is more nearly complete at the higher pressure.

EXAMPLE 3

Removal of Sulfur-Containing Impurities

A test was run to evaluate the removal of sulfur bearing lubricating oil from synthesis gas utilizing the scrubber described in Example 1. The lubricating oil contained 2,055 ppm sulfur. The addition of oil was at a rate such that the sulfur content in the reactor would increase by 26 ppm per day if all the sulfur entered the reactor. During the 6 days of oil addition, the sulfur content in the reactor was unchanged. These data indicate the scrubber utilizing product aldehydes as absorption liquid will stop sulfur bearing oil from entering the reactor.

EXAMPLE 4

Removal of Iron-Containing Impurities

A test was run to evaluate removal of iron carbonyl from synthesis gas utilizing the scrubber described in Example 1. A solution of iron-pentacarbonyl in butyraldehyde was added to the high pressure synthesis gas feed line between the compressor and the molecular oxygen scrubber. The scrubber temperature was 55° C. at the base. Scrubber pressure was about 19-bar. The iron containing solution was added continuously at a rate of about 0.04 gram of iron per hour for 72 hours. During this time a total of 0.024 gram iron accumulated in the reactor. This indicates that the scrubber removed 99.2 percent of the iron from the incoming synthesis gas.

EXAMPLE 5

Recovery and Recycle of Unreacted Propylene From Crude Hydroformylation Product Stream A test was run to evaluate desorption of low boilers from the crude product aldehydes using the apparatus described in Example 1. The crude product aldehydes were contacted at 14 bar and 55° C. with incoming synthesis gas. The crude aldehydes collected in Vessel 51 were then reduced in pressure to 0.5 bar and heated to 90° C. to force the dissolved low boilers to flash from the liquid to form a low pressure recycle stream.

In a comparison run, the crude product aldehydes were removed from the Reactor 19, passed directly to flash Chamber 27, then reduced in pressure from 14 bar to 0.5 bar, and heated to 90° C. to force dissolved synthesis gas and propylene to flash from the crude product aldehydes. These flashed gases make up the low pressure recycle.

The results of these runs are summarized in Table 2.

TABLE 2

|   | Comparison Low Pressure Recycle | Invention Recycle |
|---|---|---|
| $H_2$ | 0.10 | 0.00 |
| CO | 0.15 | 0.03 |
| $N_2$ | 0.07 | 0.00 |
| $C_3H_8$ | 1.02 | 0.01 |
| $C_3H_6$ | 9.57 | 0.11 |
| TOTAL, Lb/Hr | 10.91 | 0.15 |

From Table 2 it is seen that the volume of low pressure recycle is very significantly reduced by contacting the crude product aldehydes with the incoming synthesis gas prior to letting down the pressure.

The invention has been described in detail with particular reference to preferred embodiments thereof, but it will be understood that variations and modifications can be effected without departure from the spirit and scope of the invention described and claimed.

I claim:

1. In a hydroformylation process for the conversion of olefins having 2 up to 20 carbon atoms to aldehydes having n+1 carbon atoms, the improvement comprising intimately contacting the carbon monoxide and hydrogen feed for said hydroformylation process with at least a portion of the aldehyde-containing product stream obtained from said hydroformylation reaction prior to introducing said carbon monoxide and hydrogen feed into the hydroformylation reaction zone.

2. A process in accordance with claim 1 wherein said intimate contacting is a countercurrent contacting of liquid oxygenated product stream and gaseous carbon monoxide and hydrogen feed.

3. A process in accordance with claim 2 wherein said countercurrent contacting is carried out at substantially the same pressure as is the hydroformylation process.

4. A process in accordance with claim 1 wherein said contacting is carried out at a temperature in the range of about 25° up to 100° C.

5. A process in accordance with claim 4 wherein said contacting is carried out at a temperature in the range of about 40° up to 65° C.

6. A process in accordance with claim 1 wherein said olefin converted in said hydroformylation process has in the range of 2 up to 8 carbon atoms.

7. A process in accordance with claim 2 wherein said olefin converted in said hydroformylation process is propylene and said oxygenated product stream comprises butyraldehyde.

8. A process in accordance with claim 2 wherein said olefin converted in said hydroformylation process is ethylene and said oxygenated product stream comprises propionaldehyde.

9. A process in accordance with claim 2 wherein said olefin converted in said hydroformylation process in a mixture of ethylene and propylene and said oxygenated product stream comprises a mixture of propionaldehyde and butyraldehyde.

10. A process in accordance with claim 1 wherein said olefin converted in said hydroformylation process is at least one butene and said oxygenated product stream comprises valeraldehydes.

11. A process for purifying a feed gas employed in a hydroformylation process for the production of aldehydes having n+1 carbon atoms from olefins having 2 up to 20 carbon atoms; wherein said feed gas comprises at least one of carbon monoxide and hydrogen;

said process comprising intimately contacting said feed gas with at least a portion of the aldehyde-containing product stream obtained from said hydroformylation process prior to introducing said feed gas into the hydroformylation reaction zone.

12. A process in accordance with claim 11 wherein said intimate contacting is a countercurrent contacting of liquid aldehyde-containing product stream and feed gas.

13. A process in accordance with claim 12 wherein said countercurrent contacting is carried out at substantially the same pressure as is the pressure of said hydroformylation process.

14. A process in accordance with claim 11 wherein said contacting is carried out at a temperature in the range of about 25° up to 100° C.

15. A process in accordance with claim 14 wherein said contacting is carried out at a temperature in the range of about 40° up to 65° C.

16. A process in accordance with claim 11 wherein the starting material subjected to said hydroformylation process is an olefin having 2 up to 8 carbon atoms.

17. A process in accordance with claim 11 wherein the starting material subjected to said hydroformylation process is selected from the group consisting of:
ethylene,
propylene,
butenes as well as mixtures of any two or more thereof.

18. A process in accordance with claim 11 wherein said aldehyde-containing product stream comprises butyraldehyde.

19. A process in accordance with claim 18 wherein said aldehyde-containing product stream further comprises propionaldehyde.

20. A process in accordance with claim 19 wherein said aldehyde-containing product stream further comprises valeraldehydes.

* * * * *